US009442123B2

(12) United States Patent
Ebinuma

(10) Patent No.: US 9,442,123 B2
(45) Date of Patent: Sep. 13, 2016

(54) HIGH-MOLECULAR-WEIGHT ADIPONECTIN MEASUREMENT METHOD

(71) Applicant: SEKISUI MEDICAL CO., LTD., Tokyo (JP)

(72) Inventor: Hiroyuki Ebinuma, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/658,531

(22) Filed: Mar. 16, 2015

(65) Prior Publication Data

US 2016/0018419 A1    Jan. 21, 2016

Related U.S. Application Data

(63) Continuation of application No. 14/056,311, filed on Oct. 17, 2013, now abandoned, which is a continuation of application No. 13/596,695, filed on Aug. 28, 2012, now abandoned, which is a continuation of application No. 12/920,190, filed as application No. PCT/JP2009/000903 on Feb. 27, 2009, now abandoned.

(30) Foreign Application Priority Data

Feb. 29, 2008    (JP) ................. 2008-049198

(51) Int. Cl.
    *G01N 33/74*    (2006.01)
(52) U.S. Cl.
    CPC ......... *G01N 33/74* (2013.01); *G01N 2333/976* (2013.01)
(58) Field of Classification Search
    None
    See application file for complete search history.

(56) References Cited

U.S. PATENT DOCUMENTS

2007/0042424 A1    2/2007    Ebinuma et al.
2007/0059357 A1    3/2007    Takagi et al.

FOREIGN PATENT DOCUMENTS

| CN | 1864067 A | 11/2006 |
|---|---|---|
| CN | 1867828 A | 11/2006 |
| CN | 1945328 A | 4/2007 |
| JP | 2005 232150 | 9/2005 |
| JP | 2006 56836 | 3/2006 |
| WO | 2005 038457 | 4/2005 |

OTHER PUBLICATIONS

Pajvani, B. Utpal et al., "Structure-Function Studies of the Adipocyte-secreted Hormone Acrp30/Adiponectin", The Journal of Biology Chemistry, vol. 278, No. 11, p. 9073-9085, (2003).
Ebinuma H. et al., "Protease-based ELISA for selective guantification of mouse high-molecular-weight adiponectin", Clinica Chemica Acta, vol. 401, p. 181-183, Nov. 21, 2008).
Hada, Yusuke et al., "Selective purification and characterization of adiponectin multimer species from human plasma", Biochemical and Biophysical Research Communications vol. 356, pp. 487-493, (2007).
Ebinuma, Hiroyuki et al., "A novel ELISA system for selective measurement of human adiponectin multimers by using proteases", Clinica Chimica Acta, vol. 372, pp. 47-53, (2006).
Hara, Kazuo et al., "Measurement of the High-Molecular Weight Form of Adiponectin in Plasma is Useful for the Prediction of Insulin Resistance and Metabolic Syndrome" Diabetes Care, vol. 29, No. 6, pp. 1357-1362, (Jun. 2006).
Tsuchida, Atsushi et al., "Peroxisome Proliferator-Activated Receptor (PPAR) α Activation Increases Adiponectin Receptors and Reduces Obesity-Related Inflammation in Adipose Tissue", Diabetes, vol. 54, pp. 3358-3370, (Dec. 2005).
Nakano, Shigeru et al., "Bezafibrate regulates the expression and enzyme activity of 11 β-hydroxysteroid dehydrogenase type 1 in murine adipose tissue and 3T3-L1 adipocytes", AM ., J., Physical Endocrinol Metab., vol. 292, pp. E1213-E1222, (Apr. 2007).
Gastgeiger et al. "Protein Identification and Analysis Tools on the ExPASy Server. "The Proteomics Protocols Handbook. Ed. John M. Walker. Humana Press (2005), pp. 571-607.
Maeda et al., "cDNA Cloning and Expression of a Novel Adipose Specific Collagen-like Factor, apM1 (Adipose Most Abundant Gene Transcript 1)", Biochem. Biophys. Res. Comm, 1996, vol. 221(2)):286-289.
Hu et al., "AdipoQ is a Novel Adipose-specific Gene Dysregulated in Obesity", JBC, 1996, 271(18) :10697-10703.
Reference sequence of human Adiponectin NP_001171271.1, http://www.ncbi.nlm.nih.gov/protein/NP_033735.3 downloaded Feb. 23, 2012.
Reference sequence of mouse Adiponectin NP_033735.3, http://www.ncbi.nlm.nih.gov/protein/NP_033735.3 downloaded. Feb. 23, 2012.
ExPasy Peptide Cutter Tool Results: human adiponectin NP_001171271.1—downloaded Feb. 23, 2012.
Expasy peptide Cutter Tool Results: mouse adiponectin NP_003735.3—downloaded Feb. 23, 2012.
Office Action issued on Jun. 23, 2014 in the corresponding Chinese Patent Application No. 200980106328.9.
Brenda EC 3.4.21.1 Chymotrypsin information <http://www.brenda-enzymes.org/php/result_flat.php4?ecno=3.4.21.1. > Retrieved Sep. 9, 2014.

*Primary Examiner* — Suzanne M Noakes
(74) *Attorney, Agent, or Firm* — Oblon, McClelland, Maier & Neustadt, L.L.P.

(57) ABSTRACT

Provided is a method of separating and measuring highly active HMW adiponectin in adiponectin multimers. A method of measuring high-molecular-weight adiponectin in a sample, wherein adiponectin multimers are separated by use of a protease and measured immunologically, the method comprising reacting a sample containing adiponectin multimers with chymotrypsin.

8 Claims, 8 Drawing Sheets

Fig. 3A  Fig. 3B  Fig. 3C 0 10 25 50 u/ml   0 10 25 50 u/ml   0 10 25 50 u/ml

HMW→
MMW→
Alb-LMW
+ LMW

MMW→

HMW→
MMW→
Alb-LMW
+ LMW

Fig. 4A

HMW→

MMW→

Alb-LMW  
+ LMW

Undigested  
Proteinase K

Fig. 4B

HMW→

MMW→

Alb-LMW  
+ LMW

Undigested  
Proteinase K

HIGH-MOLECULAR-WEIGHT ADIPONECTIN MEASUREMENT METHOD

TECHNICAL FIELD

The present invention relates to a method of separating and immunologically measuring a high-molecular-weight (HMW) fraction in adiponectin multimers contained in a biological sample.

BACKGROUND ART

Adiponectin is a hormone which is produced and secreted specifically in fatty tissue and having anti-diabetes and anti-arteriosclerosis activity, and is present in blood at a relatively high level. In recent years, hypoadiponectinemia associated with obesity, particularly caused by accumulation of visceral fat, is thought to trigger onset of diabetes, arteriosclerotic diseases or hypertension.

Structurally, adiponectin belongs to the Clq (Complement lq) family and has a collagen-like domain which is intrinsic to the Clq family. A study has reported that adiponectin forms a multimer mainly composed of trimers. Recently, the present inventors have revealed the structure of adiponectin multimers present in human blood (trimer including albumin-bound trimer, hexamer, and HMW fraction), and have reported that, among adiponectin multimers, HMW adiponectin exhibits the highest activation represented by phosphorylation activity on AMPK (adenosine monophosphate activated protein kinase) which promotes glucose intake and fatty acid metabolism (Non-Patent Document 1). In addition, the inventors disclosed a method of directly determining the HMW adiponectin level and indirectly determining the level of a trimer fraction or a hexamer fraction, respectively, in which a biological sample containing human-derived adiponectin multimers is reacted with a specific type of protease to selectively digest fractions other than the target fraction and remaining adiponectins are immunologically assayed (Patent Document 1 and Non-Patent Document 2).

A clinical study on adiponectin multimers in diabetes groups and coronary artery disease groups through employment of the selective assay system has revealed that the ratio of HMW adiponectin level to total adiponectin level (HMWR) is a more sensitive and specific prophetic index for insulin resistance and metabolic syndrome than is the total adiponectin level (Non-Patent Document 3). Thus, not only an assay of the total adiponectin level but also a selective assay of fractions is envisaged to be clinically useful.

Meanwhile, among therapeutic drugs for metabolic-syndrome-related diseases (diabetes, hypertension, and hyperlipidemea), some drugs increase adiponectin, and are of interest. For example, a thiazolidine derivative, which is an insulin resistance ameliorating agent, increases HMW adiponectin (Non-Patent Document 4). In addition, recently, a drug categorized as an angiotensin receptor antagonist which is used as a hypotensive drug and some therapeutic agents for hyperlipidemea are reported to increase adiponectin (Non-Patent Document 5). Thus, adiponectin is expected to ameliorate insulin-resistance which is frequently observed in disease groups involving metabolic syndrome.

As described above, adiponectin-increasing action is of great value in the development of drugs for metabolic-syndrome-related diseases. In addition to the drug development, adiponectin attracts attention in the field of healthy food, and research and development of functional food having adiponectin-increasing action is extensively carried out.

Generally, the efficacy and effect of a drug or a functional food is assessed primarily through experiments by use of experimental animals such as mice and rats. Regarding adiponectin-increasing action, the change in the blood adiponectin level of the experimental animal is effectively employed as an index (see, for example, Patent Documents 2 and 3). The adiponectin level in samples of a mouse or a rat is available by means of a commercially available assay kit. However, currently available kits can only determine the total adiponectin level but cannot selectively determine levels of adiponectin multimers. Particularly, there is demand for a fractional assay method for highly active HMW adiponectin.

The present inventors found a method of selectively assaying adiponectin multimers in which adiponectin multimers present in a human biological sample are reacted with a specific type of protease (Patent Document 1 and Non-Patent Document 2). Interestingly, the inventors found that when the protease used in the method was applied in an assay of mouse-derived adiponectin multimers, precise results were not obtained particularly for assaying an HMW fraction.

Pajvani et al. reported digestion specificity of trypsin on recombinant mouse-derived adiponectins. According to this report, trypsin digests a low-molecular-weight fraction (LMW) and does not digest a middle-molecular-weight fraction (MMW) or an HMW fraction. Thus, trypsin is not suited for selective measurement of HMW adiponectin (Non-Patent Document 6).

PRIOR ART DOCUMENT

Patent Document 1: International Publication WO 2005/038457
Patent Document 2: JP-A-2005-232150
Patent Document 3: JP-A-2006-56836
Non-Patent Document 1: Hada Y et al., Biochem. Biophys. Res. Commun. 356: 487-493, 2007
Non-Patent Document 2: Ebinuma H et al., Clinica Chimica Acta 372: 47-53, 2006
Non-Patent Document 3: Hara K et al., Diabetes Care 29: 1357-1362, 2006
Non-Patent Document 4: Tsuchida A et al., Diabetes 54: 3358-3370, 2005.
Non-Patent Document 5: Nakano S et al., Am. J. Physiol. Endocrinol. Metab. 292: 1213-1222, 2007
Non-Patent Document 6: Pajvani UB et al., J. Biol. Chem. 278: 9073-85, 2003

DISCLOSURE OF THE INVENTION

Problems to be Solved by the Invention

An object of the present invention is to provide a method of selectively measuring highly active HMW adiponectin in adiponectin multimers.

Means for Solving the Problems

The present inventors have carried out extensive studies in order to solve the aforementioned problems, and have found that through reacting chymotrypsin, among a variety of proteases, on a sample containing adiponectin multimers, adiponectins other than HMW fraction adiponectin can be selectively digested even in a sample derived from mice, rats, etc, and that HMW adiponectin can be selectively measured by immunologically assaying the HMW adiponectin remaining after the digestion by chymotrypsin.

Accordingly, the present invention provides a method of selectively measuring high-molecular-weight adiponectin in a sample, wherein adiponectin multimers are separated by use of a protease and measured immunologically, the method including reacting a sample containing adiponectin multimers with chymotrypsin.

Effects of the Invention

According to the present invention, HMW adiponectin in adiponectin multimers derived not only from human but also from mice, rats, and other animals can be selectively assayed, and thus the potentiating effect of the developed drugs, functional foods, etc. on adiponectin can be evaluated more precisely.

BRIEF DESCRIPTION OF THE DRAWINGS

FIG. 3A: A chart showing digestion specificity of trypsin to adiponectin multimers derived from mouse serum.

FIG. 3B: A chart showing digestion specificity of trypsin to adiponectin multimers derived from rat serum.

FIG. 3C: A chart showing digestion specificity of trypsin to adiponectin multimers derived from human serum.

FIG. 4A: A chart showing digestion specificity of proteinase K to adiponectin multimers derived from human serum.

FIG. 4B: A chart showing digestion specificity of proteinase K to adiponection multimers derived from mouse serum.

MODES FOR CARRYING OUT THE INVENTION

Figure 1:
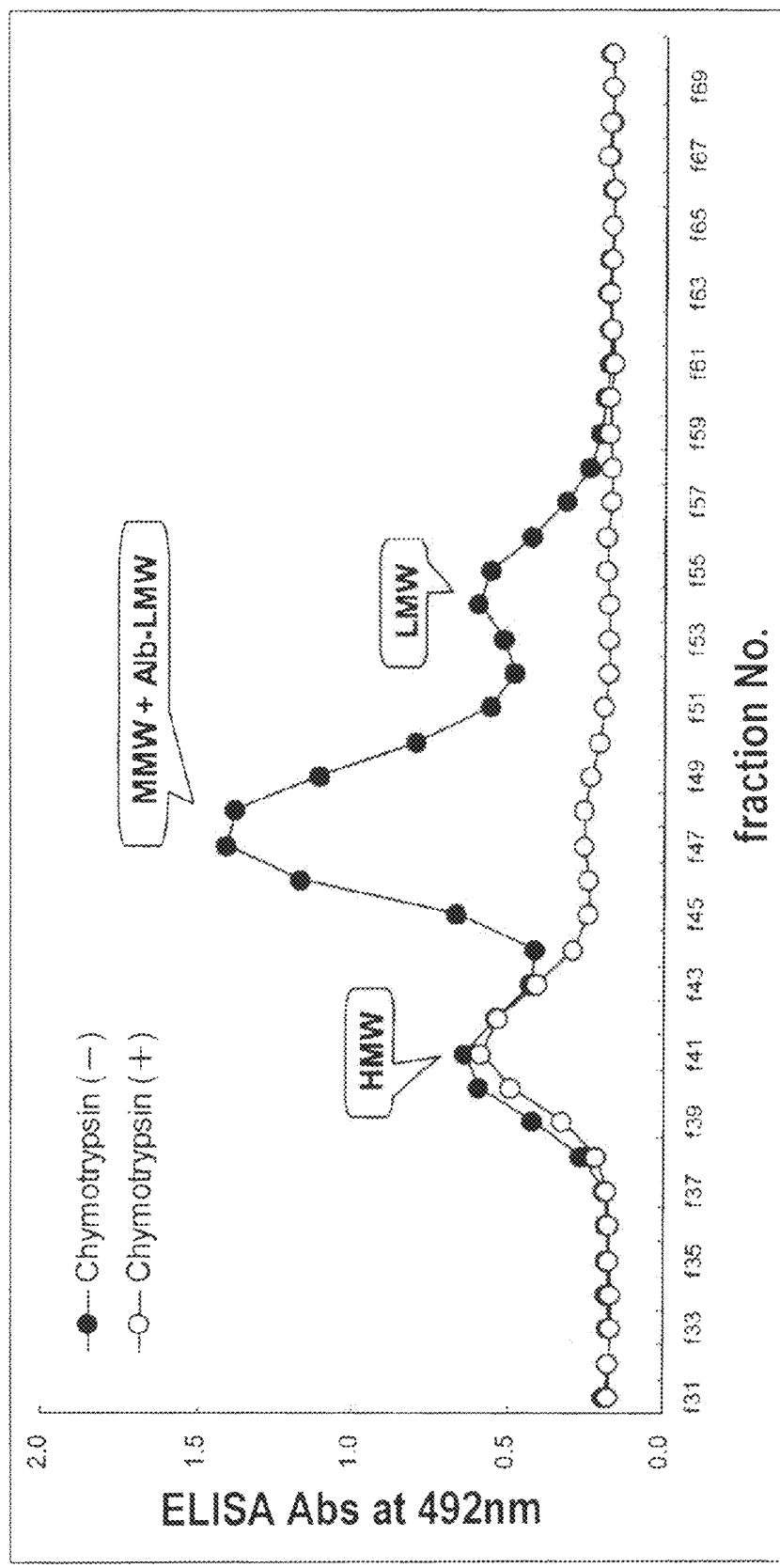
FIG. 1: A chart showing digestion specificity of chymotrypsin to adiponectin multimers derived from mouse.

No particular limitation is imposed on the sample which can be employed in the present invention, so long as the sample contains adiponectin multimers derived from mammal. Examples of the sample derived from mammal include body fluids such as blood, urine, etc. and extracts of tissue derived from mammal, and culture supernatants of cells derived from the tissue. Examples of the mammal include rodents such as mice and rats; and human. Among them, blood samples (serum and plasma) of mice and rats, in particular, mouse blood samples, are preferred as samples for evaluating the potentiating effect of the developed drugs, functional foods, etc. on adiponectin more precisely. Also, blood samples (serum and plasma) of human are preferred as samples for diagnosing diabetes or other diseases.

The method of separating HMW adiponectin and immunologically measuring the same will next be described. A sample containing adiponectin multimers is reacted with chymotrypsin to thereby digest adiponectins other than HMW fraction. Then, the HMW adiponectin remaining after the digestion by chymotrypsin is immunologically assayed by use of an anti-adiponectin antibody. The chymotrypsin which may be employed in the present invention may be a purified commercial product, or a roughly purified product having such a purification degree that the effect of the present invention is not impaired. Alternatively, chymotrypsin produced through a recombinant technique may be used. So long as the enzyme has a chymotrypsin activity, the enzyme may be chemically modified.

The treatment of a biological sample with chymotrypsin is preferably performed in a buffer such as a phosphate buffer, a Tris buffer or a Good's buffer, at 4 to 60° C. (more preferably 4 to 45° C.) for 5 minutes to 24 hours. The concentration of chymotrypsin employed in the treatment, which depends on factors such as reaction temperature and reaction time, is generally 0.1 to 1000 u/mL, preferably 1 to 100 u/mL. The chymotrypsin concentration, reaction temperature, and reaction time in the chymotrypsin treatment depend on the type of the animal from which the samples are derived. Thus, through a preliminary test, conditions under which merely HMW adiponectin contained in the samples is not digested are preferably confirmed. The enzymatic activity of chymotrypsin (u) refers to the amount of chymotrypsin required for hydrolyzing 1 μmol of N-benzoyl-L-tyrosine ethyl ester (BTEE) per minute at a pH of 7.8 and 25° C.

Among adiponectin multimers in the sample pretreated with chymotrypsin, HMW adiponectin remains after the chymotrypsin digestion. Thus, when the adiponectin level of the sample is determined through immunological assay by use of an anti-adiponectin antibody, only HMW adiponectin can be selectively measured. Therefore, the immunological assay of the sample treated with chymotrypsin may be conducted with an anti-adiponectin antibody through a generally-employed immunological technique.

The antibody for assaying HMW adiponectin in the sample remaining after chymotrypsin treatment may be an antibody which recognizes adiponectin. The anti-adiponectin antibody employed may be a monoclonal antibody or a polyclonal antibody and may be obtained by immunizing an appropriate animal through a known technique. Alternatively, a commercial available antibody may also be used in the present invention. Examples of the antibody include: the anti-mouse adiponectin antibody including "Anti-mouse Adiponectin monoclonal antibody" and "Anti-mouse Adiponectin polyclonal antibody, Goat" (products of R&D Systems); "Anti-mouse Adiponectin, mAd (MADI04)" (product of AdipoGen); and "Anti-mouse Adiponectin monoclonal antibody" (products of CHEMICON); the anti-rat adiponectin antibody including "Anti-rat Adiponectin polyclonal antibody, Goat" (product of R&D Systems), and "Anti-rat Adiponectin monoclonal antibody" and "Anti-rat Adiponectin polyclonal antibody, Rabbit" (products of CHEMICON); and the anti-human adiponectin antibody including Goat α human Acrp 30 antibody (product of COSMO BIO, GT), rabbit α hu adiponectin-PoAb (product of COSMO BIO, Chemicon), hu Acrp30-MoAb (product of Fujisawa Pharmaceutical Co., Ltd., BD), Mouse α hu Adiponectin MoAb (product of COSMO BIO, Chemicon), and anti-human ACRP 30 monoclonal antibody (AX773, AX741, Ne, Na; products of Wako Pure Chemical Industries, Ltd.). These antibodies may be used alone or in appropriate combination. Alternatively, a commercial available kit for assaying the total adiponectin level may also be employed. Still alternatively, there may be employed an immunological assay method established by the present inventors (WO 2005/038458), which method includes reacting adiponectins contained in a biological sample with one or more members selected from a reducing agent, an acid or a salt thereof, a surfactant and a protease other than chymotrypsin to convert adiponectin multimers to a certain specific form; and immunological assaying the converted product.

In the immunological assay method employed in the present invention, an antibody which binds specifically to adiponectin is bound to an insoluble carrier, to thereby capture adiponectin thereon, and the presence or absence (qualitative), or the amount of adiponectin present in the sample is determined. Examples of the assay method employed in the present invention include LTIA (latex turbidimetric immunoassay), ELISA (enzyme-linked immunosorbent assay), CLEIA (chemiluminescent enzyme-linked immunosorbent assay), RIA (radioimmunoassay), etc. Among them, using LTIA, the presence or absence (qualitative), or the amount of adiponectin present is determined by combining an insoluble carrier bearing an antibody which binds specifically to adiponectin with HMW adiponectin remaining after chymotrypsin treatment to cross-link (agglutinate) the insoluble carrier through the adiponectin, and optically measuring the turbidity of the sample caused by the cross-linking. LTIA is preferably employed for easily, rapidly and precisely measuring HMW adiponectin The insoluble carrier employed in the present invention is an organic insoluble carrier which is employed as a commonly used immunological assay reagent and which can be industrially produced in large scale. In LTIA, polystyrene latex particles, which have excellent adsorption property for antibodies and which can maintain stable biological activity for a long period of time, are preferred. In ELISA, a 96-well microplate made of polystyrene or a similar material is preferred.

A variety of techniques for immobilizing an antibody on the surface of the aforementioned insoluble carrier are known and may be appropriately employed in the present invention. Examples of the immobilizing (immunizing) method include a method in which an antibody is physically adsorbed on the surface of the insoluble carrier and a method in which an antibody is effectively immunized on the surface of the insoluble carrier bearing a functional-group with a known physical or chemical binding method.

No particular limitation is imposed on the conditions of reaction between the antibody-bearing insoluble carrier and adiponectin, so long as antigen-antibody reaction can be occurred. Any reaction solutions may be employed so long as adiponectin and the antigen can be reacted in the solution. Appropriate components may be dissolved in the solution, including buffer components for regulating pH such as a phosphate buffer, a glycine buffer, a Tris buffer and a Good's buffer; surfactants and sodium chloride for preventing non-specific reaction; stabilizers such as bovine serum albumin, sucrose, and high-molecule polysaccharides; and additives other than the aforementioned substances for controlling reactivity, including water-soluble polysaccharides such as dextran, a reducing agent, an acid-neutralizing agent and a protease-inactivator.

In the aforementioned LTIA or ELISA, the following detection methods are employed. In LTIA, no particular limitation is imposed on the method for measuring the degree of agglutination of the insoluble carrier. For example, in the case where the degree of agglutination is qualitatively or semi-quantitatively determined, the degree of agglutination can be visually determined by comparing the turbidity of a sample of known concentration with that of the sample of interest. In the case of quantitative determination of the degree of agglutination, optical measurement is preferred, from the viewpoints of easiness and precision of the measurement. Optical measurement of agglutination may be performed through a known method. More specifically, there may be employed a variety of methods such as turbidimetry, in which formation of aggregate is detected as an increased level of the turbidity; particle size distribution, in which formation of aggregate is reflected by change in particle size distribution or mean particle size; and integral sphere turbidimetry, in which a change in forward scattering light caused by formation of aggregate is measured by means of an integral sphere-, and the intensity ratios of the scattering light to transmitting light are compared. In ELISA, no particular limitation is imposed on the method for determining the reaction product formed through the enzymatic activity of the enzyme-labeled antibody. For example, the absorbance at the intrinsic wavelength of the product produced from the enzymatic reaction (e.g., in the case where the enzymatic activity of an HRP-labeled antibody is detected by use of o-phenylenediamine hydrochloride and hydrogen peroxide as substrates, absorbance at 492 nm) may be detected by means of a 96-well-microplate-reader.

Furthermore, when the biological sample is not subjected to chymotrypsin treatment, the total adiponectin level is obtained. Thus, the ratio of HMW adiponectin level, which is calculated through chymotrypsin treatment, to total adiponectin level can be calculated in a simple manner.

EXAMPLES

The present invention will next be described in detail by way of examples, which should not be construed as limiting the invention thereto.

Example 1

Digestion Specificity to Adiponectin Multimers in Mouse Serum

α-Chymotrypsin (Type I-S; No. C7762, product of Sigma-Aldrich) was dissolved in 50 mM Tris-HCl buffer (pH: 8.0), to thereby prepare an enzyme solution having a concentration of 10 u/mL, and the enzyme solution (100 μL) was added to mouse serum (10 μL). The mixture was incubated at 37° C. for 20 minutes. To the reaction mixture, BSA-PBST (20mM phosphate buffer containing 1% bovine serum albumin and 0.05% Tween 20, pH: 7.2) (400 μL) was added. The entire mixture was subjected to gel filtration chromatography by means of Superdex 200 (product of GE Healthcare Bio-Sciences). PBS (20 mM phosphate buffer, pH: 7.2) was used as an eluent, and fractions (1 mL each) were collected. As controls, fractions obtained through gel filtration chromatography under the same conditions except that no chymotrypsin was added, were used.

Detection of adiponectin in each fraction was performed in the following manner. An anti-mouse adiponectin monoclonal antibody (product of R&D Systems) was diluted with PBS to a concentration of 2.5 μg/mL, and added to an ELISA plate at 50 μL/well to sensitize the plate overnight. The plate was washed with PBST (PBS containing 0.05% Tween 20, pH: 7.4) and blocked by adding BSA-PBST (100

μL) to the washed plate. Subsequently, each fraction was two-fold diluted with BSA-PBST, and a portion thereof (50 μL) was added to the plate to be reacted at room temperature for one hour. The plate was washed with PBST, and a goat anti-mouse adiponectin polyclonal antibody (product of R&D Systems) which had been diluted with BSA-PBST to 1.0 μg/mL (50 μL) was added to the washed plate to react the mixture at room temperature for one hour. The plate was washed with PBST, and a rabbit anti-goat Ig's HRP-labeled antibody solution (product of DAKO) which had been 2,000-fold diluted with BSA-PBST (50 μL) was added to the washed plate to react the mixture at room temperature for one hour. The plate was washed with PBST, and a substrate solution (250 mM citrate buffer containing 2 mg/mL o-phenylenediamine hydrochloride and 0.02% hydrogen peroxide, pH: 5.0) (50 μL) was added to the washed plate to react the mixture at room temperature for 10 minutes. A stop solution (1.5N sulfuric acid, 1 mM EDTA-2Na) (50 μL) was added to the plate so as to stop the reaction, and the absorbance at 492 nm was measured. The results are shown in FIG. 1.

The adiponectin multimers present in the mouse serum which had not been subjected to chymotrypsin digestion were separated into three peaks. In contrast, the sample in which the mouse serum was treated with chymotrypsin did not exhibit the elution peak for MMW adiponectin (second peak) including the elution peak for albumin-bound (Alb-) LMW, or the elution peak for LMW adiponectin (third peak), but exhibited the elution peak for HMW adiponectin (first peak). As a result, through reacting chymotrypsin on a sample containing mouse-derived adiponectin multimers, only HMW adiponectin can be maintained without being digested. Therefore, through assaying the adiponectin level in the solution thus treated, the level of the HMW adiponectin can be calculated.

Example 2

Digestion Specificity to Adiponectin Multimers in Rat Serum

α-Chymotrypsin- (Type I-S; No. C7762, product of Sigma-Aldrich) was dissolved in 50 mM Tris-HCl buffer (pH: 8.0), to thereby prepare an enzyme solution having a concentration of 100 u/mL, and the enzyme solution (100 μL) was added to rat serum (50 μL). The mixture was incubated at 37° C. for 20 minutes. To the reaction mixture, BSA-PBST (400 μL) was added. The entire mixture was subjected to gel filtration chromatography by means of Superdex 200 (product of GE Healthcare Bio-Sciences). PBS was used as an eluent, and fractions (1 mL each) were collected. As controls, fractions obtained through gel filtration chromatography under the same conditions except that no chymotrypsin was added, were used.

Figure 2:
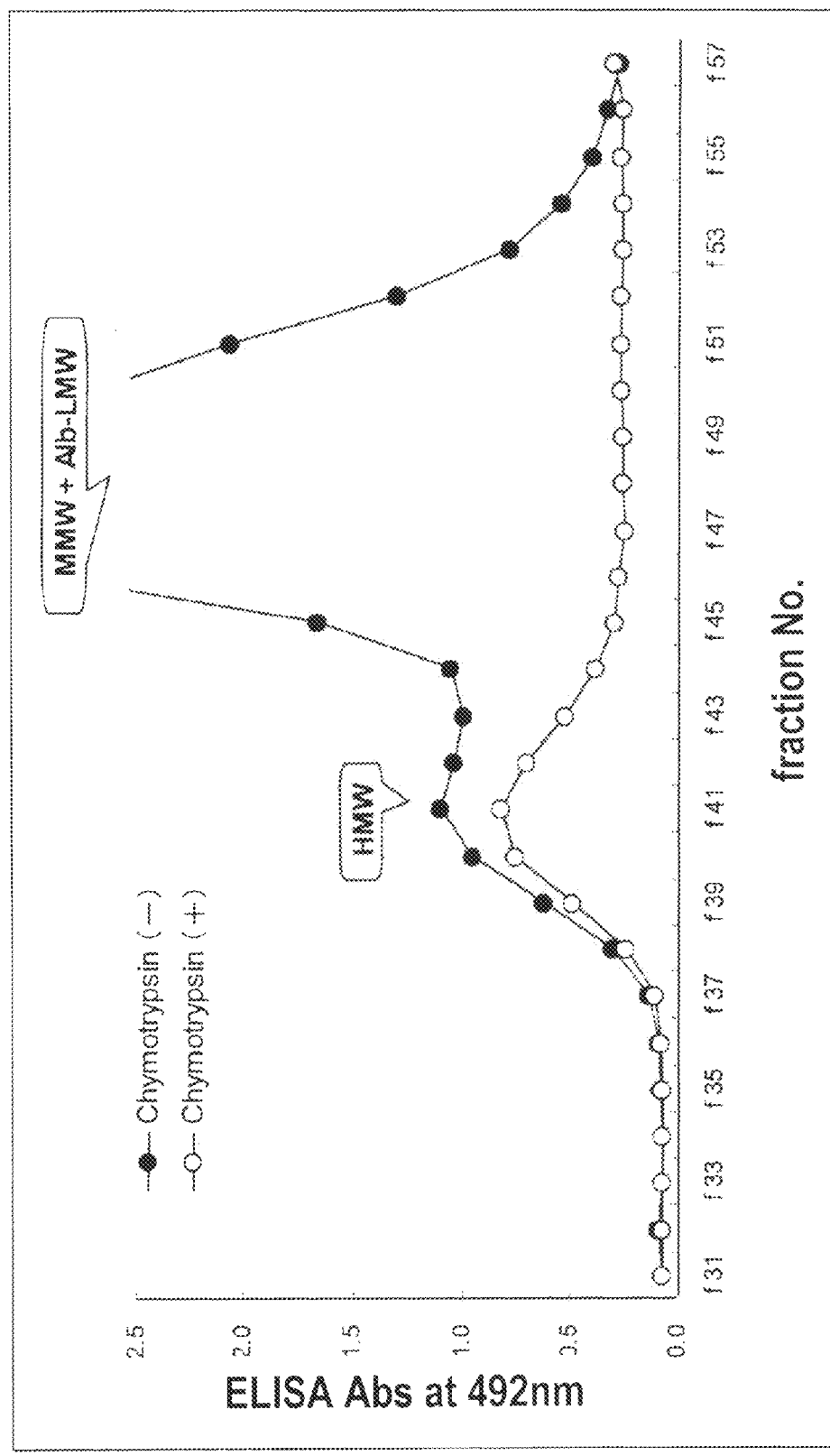
FIG. 2: A chart showing digestion specificity of chymotrypsin to adiponectin multimers derived from rat.

Detection of adiponectin in each fraction was performed in the following manner. A goat anti-rat adiponectin polyclonal antibody (product of R&D Systems) was diluted with PBS to a concentration of 0.5 μg/mL, and added to an ELISA plate at 50 μL/well to sensitize the plate overnight. The plate was washed with PBST and blocked by adding BSA-PBST (100 μL) to the washed plate. Subsequently, each fraction was two-fold diluted with BSA-PBST, and a portion thereof (50 μL) was added to the plate to be reacted at room temperature for one hour. The plate was washed with PBST, and a rabbit anti-mouse globular adiponectin polyclonal antibody (WO 2005/038457) which had been diluted with BSA-PBST to 1.0 μg/mL (50 μL) was added to the washed plate to react the mixture at room temperature for one hour. The plate was washed with PBST, and a goat anti-rabbit Ig's HRP-labeled antibody solution (product of BIOSOUCE) which had been 2,000-fold diluted with BSA-PBST (50 μL) was added to the washed plate to react the mixture at room temperature for one hour. The plate was washed with PBST, and a substrate solution (250 mM citrate buffer containing 2 mg/mL o-phenylenediamine hydrochloride and 0.02% hydrogen peroxide, pH: 5.0) (50 μL) was added to the washed plate to react the mixture at room temperature for 10 minutes. A stop solution (1.5N sulfuric acid, 1mM EDTA-2Na) (50 μL) was added to the plate so as to stop the reaction, and the absorbance at 492 nm was measured. The results are shown in FIG. 2.

The sample adiponectin multimers present in the rat serum which had not been subjected to chymotrypsin digestion were separated into two peaks, and very weak elution peak was observed for HMW adiponectin (first peak). The sample in which the rat serum was treated with chymotrypsin did not exhibit the elution peak for MMW adiponectin (second peak) including the elution peak for albumin-bound (Alb-) LMW, while exhibited the elution peak for HMW adiponectin (first peak). As a result, through reacting chymotrypsin on a sample containing rat-derived adiponectin multimers, only HMW adiponectin can be maintained without being digested. Therefore, through assaying the adiponectin level in the solution thus treated, the level of the HMW adiponectin can be calculated.

Referential Example 1

Digestion Specificity to Adiponectin Multimers when Trypsin was Used

Trypsin (No. T1426, product of Sigma-Aldrich) was dissolved in 50 mM Tris-HCl buffer (pH: 8.0), to thereby prepare enzyme solutions having a concentration of 0 to 50 u/mL, and each enzyme solution (100 μL) was added to mouse serum, rat serum, and human serum (10 μL each). Each mixture was incubated at 37° C. for 20 minutes. To the reaction mixture, BSA-PBST (400 μL) was added. A portion of the mixture was separated through native polyacrylamide gel electrophoresis (native-PAGE) and transferred to PVDF membrane through semi-dry blotting, followed by immunostaining. In a specific procedure, the transferred membrane was blocked with BSA-PBST and washed with PBST. Then, a goat anti-mouse adiponectin polyclonal antibody (product of R&D systems) (0.1 μg/mL) was reacted with the membrane at room temperature for one hour. The membrane was sufficiently washed with PBST, and color development was performed by use of Vector ABC kit (Goat) and a DAB substrate kit (product of Funakoshi). FIGS. 3A-3C show the results of immunostaining of the tested sera (FIG. 3A: mouse, FIG. 3B: rat, FIG. 3C: human).

When the trypsin activity is 0 u/mL, adiponectins were separated to an HMW fraction, a hexamer (MMW) fraction, and a trimer fraction (LMW) containing an albumin-bound trimer (Alb-LMW), which are shown in each electrophoresis pattern from the start point of electrophoresis (in the case of rat serum, an MMW fraction is predominantly observed, and HMW and LMW fractions were not observed as clearly stained bands). After digestion with a trypsin activity of 10 to 50 u/mL, the LMW fraction was digested, but the MMW and HMW fractions could not be digested. Therefore, it was indicated that trypsin is not available for selectively assaying HMW adiponectin in an animal serum.

Referential Example 2

Digestion Specificity to Adiponectin Multimers when Proteinase K was Used

Human serum or mouse serum was digested in the manner similar to Referential Example 1, except that the protease was changed to 7.5 u/mL of proteinase K. A portion of the reactant was immunostained (FIG. 4A: human, FIG. 4B: mouse).

In the case of human serum, only the HMW fraction remained without being digested. However, in the case of mouse serum, all the fractions including the HMW fraction were digested. Therefore, it was indicated that proteinase K is not available for selectively assaying HMW adiponectin in an animal serum.

Example 3

Digestion Specificity to Adiponectin Multimers in Human Serum

Figure 5B:
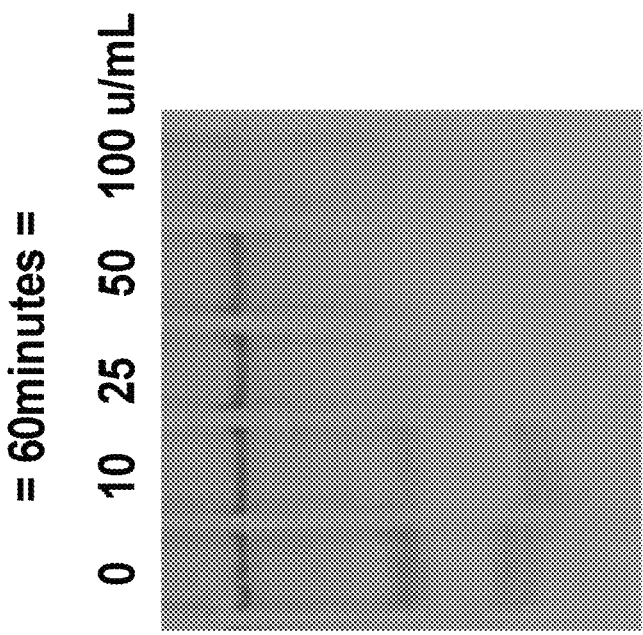
FIG. 5B: A chart showing digestion specificity of chymotrypsin to adiponectin multimers derived from human, where the chymotrypsin digestion time was 60 minutes.
Figure 5A:
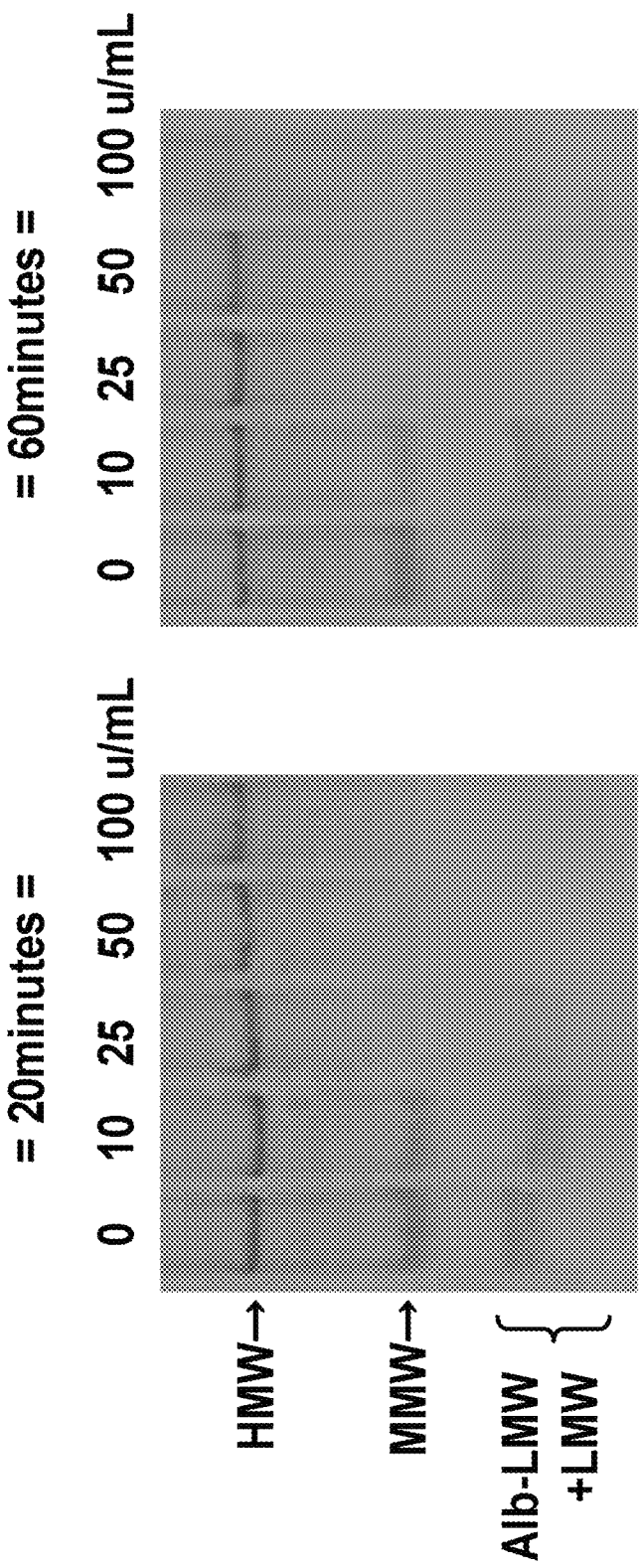
FIG. 5A: A chart showing digestion specificity of chymotrypsin to adiponectin multimers derived from human, where the chymotrypsin digestion time was 20 minutes.

Chymotrypsin (Type II; No. C4129, product of Sigma-Aldrich) was dissolved in 50 mM Tris-HCl buffer (pH: 8.0), to thereby prepare enzyme solutions having a concentration of 0 to 100 u/mL, and each enzyme solution (100 μL) was added to human serum (10 μL). The mixture was incubated at 37° C. for 20 minutes or 60 minutes. To the reaction mixture, BSA-PBST (400 μL) was added. A portion of the mixture was separated through native polyacrylamide gel electrophoresis (native-PAGE) and transferred to PVDF membrane through semi-dry blotting, followed by immunostaining. In a specific procedure, the transferred membrane was blocked with BSA-PBST and washed with PBST. Then, a goat anti-mouse adiponectin polyclonal antibody (product of R&D systems) (0.1 μg/mL) was reacted with the membrane at room temperature for one hour. The membrane was sufficiently washed with PBST, and color development was performed by use of Vector ABC kit (Goat) and a DAB substrate kit (product of Funakoshi). FIGS. 5A and 5B show the results of immunostaining.

In the case where the chymotrypsin digestion time was 20 minutes, small amounts of MMW or smaller-molecular-weight fractions still remained after the digestion with chymotrypsin at a concentration of 25 u/mL, while only HMW was remained after the digestion with chymotrypsin at a concentration of 50 to 100 u/mL. However, in the case where the chymotrypsin digestion time was 60 minutes, no substantial digestion occurred by chymotrypsin of 10 u/mL, only HMW was remained after the digestion with chymotrypsin at a concentration of 25 to 50 u/mL, and all the fractions including HMW were digested after the digestion with chymotrypsin at a concentration of 100 u/mL.

Referential Example 3

Purification of Adiponectin Multimers Derived from Mouse Serum (Ms-mAd)

Mouse serum (180 mL) was added to anti-mouse globular adiponectin antibody-bound resin (WO 2005/038457), and the resin was washed with 100 mM Tris-HCl buffer containing 0.5M NaCl (pH: 8.5) and further washed with 100 mM acetate buffer containing 0.5M NaCl (pH: 5.0). Subsequently, mouse adiponectin fractions were eluted by use of 100 mM glycine-HCl buffer (pH: 2.5), and each eluted fraction was neutralized with a ¹⁄₁₀ amount of 2M Tris-HCl buffer (pH: 8.0). The neutralized eluted fraction was added to Protein A resin, and a fraction not adsorbed by Protein A resin was recovered as a purified Ms-mAd. The purified fraction was dialyzed against PBS, and the adiponectin content was measured by means of a "mouse/rat adiponectin ELISA kit" (product of Otsuka Pharmaceutical Co., Ltd.).

Referential Example 4

Preparation of Anti-mouse Adiponectin Rat Monoclonal Antibody

The purified Ms-mAd (50 μg) prepared in Referential Example 3 was mixed with an equiamount of Freund's complete adjuvant. Rats (F344/Jcl) were immunized twice with the mixture with an interval of two weeks. The spleen and lymph node cells were removed from each of the immunized rats, and the cells were fused with sp2/o myeloma cells through a conventional method employing polyethylene glycol. Fused cells which produce anti-mouse adiponectin monoclonal antibody were selected through selecting a well exhibiting high reactivity with recombinant mouse adiponectin (rMs-Ad) (product of BioVender) by means of ELISA, followed by limiting dilution. Anti-mouse adiponectin monoclonal antibody was recovered through administering the selected fused cells to the abdominal cavity of each of the pristan-treated nude mice and collecting ascites. A specific antibody (IgG) obtained from the ascites was purified by collecting precipitates in 50% saturated ammonium sulfate followed by dialyzing against 20 mM Tris-HCl buffer (pH: 8.0), adding the product to DEAE ion-exchange resin (Product of Tosoh Corporation), and eluting the antibody with NaCl solution with concentration-gradient (0 to 200 mM), whereby purified IgG (MoAb83201R) was recovered.

Referential Example 5

Preparation of Anti-mouse Adiponectin Rabbit Polyclonal Antibody and Biotin-Labeling Thereof The purified Ms-mAd (120 μg) prepared in Referential Example was mixed with an equiamount of Freund's complete adjuvant. Rabbits were immunized five times with the mixture with intervals of two weeks, to thereby produce an antiserum. A specific antibody (IgG) in the antiserum was purified through a conventional method employing Melon Gel (product of Pierce). Subsequently, EZ-Link Sulfo-NHS-LC-Biotin (product of Pierce) was added to the purified IgG, to thereby perform biotin-labeling (biotinylated PoAb).

Example 4

Comparison of ELISA Method and Gel Filtration Separation Method for Determination of Total Amount of Mouse Adiponectin and HMW 1-1) Pre-treatment of Samples For HMW assay: A protease solution (50 mM Tris-HCl buffer, pH: 8.0) containing chymotrypsin (35 u/mL) (100 μL) was added to each mouse serum (n=10) (10 μL), and the mixture was incubated at 37° C. for 20 minutes. Then, a treatment solution (100 mM borate buffer, pH: 11.0) (700 μL) was added thereto, to thereby provide a treated sample solution for HMW assay.

For total level assay: A protease solution containing no chymotrypsin (100 μL) was added to mouse serum (10 μL), and a treatment solution (700 μL) was added thereto, to thereby provide a treated sample solution for total level assay.

1-2) ELISA Method

The anti-mouse adiponectin monoclonal antibody (83201R) prepared in Referential Example 4 diluted with PBS to a concentration of 5 μg/mL was placed in an ELISA plate for sensitization. Subsequently, the plate was blocked with BSA-PBST. Each of the pre-treated sample solution was 101-fold diluted with BSA-PBST and added to the plate in a volume of 50 μL followed by reacting at room temperature for one hour. The plate was washed with PEST, and the biotin-labeled anti-mouse adiponectin polyclonal antibody (Biotinylated PoAb) (50 μL) prepared in Referential Example 5 was added to the plate, followed by reacting at room temperature for one hour. The plate was washed with PEST, and HRP-avidin which had been 2,000-fold diluted with BSA-PBST was added to the plate, followed by reacting at room temperature for 30 minutes. The plate was washed with PEST, and color development was performed by use of an OPD color-developing solution (containing 2 mg/mL o-phenylenediamine hydrochloride and 0.02% hydrogen peroxide, in 250 mM citrate buffer, pH: 5.0). A stop solution (1.5N sulfuric acid, 1 mM EDTA-2Na) was added to the plate so as to stop the reaction, and the absorbance at 492 nm was measured. By use of a recombinant mouse adiponectin (rMs-Ad) as a standard, the adiponectin level of each sample was calculated.

2) Gel Filtration Separation Method

Figure 6:
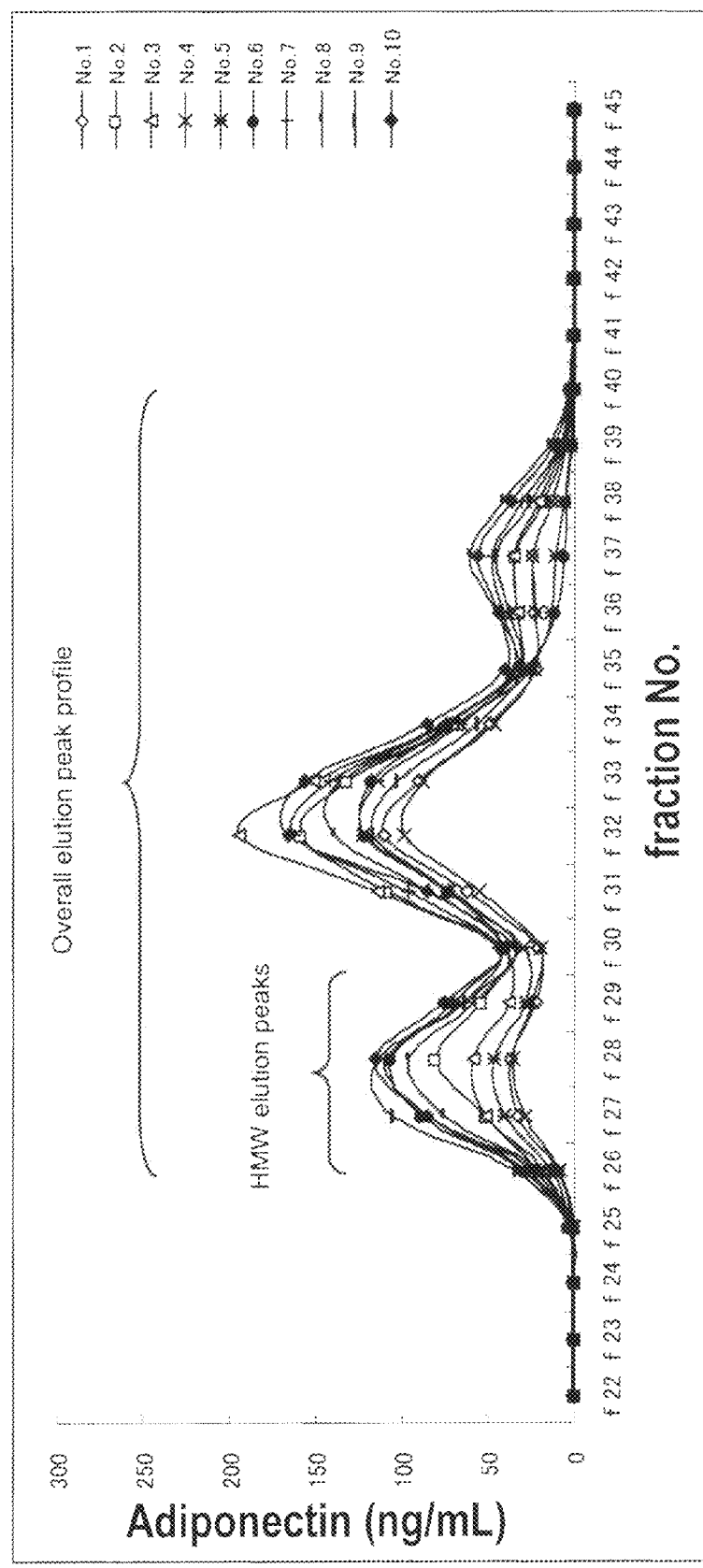
FIG. 6: A chart showing results from gel filtration separation of mouse high-molecular-weight adiponectins.

Each of the same mouse serum samples (n=10) as employed in the aforementioned 1-1) (50 μL) was subjected to gel filtration chromatography under the same conditions as employed in Example 1, to thereby provide fractions. Each fraction was 21-fold diluted with BSA-PBST, and adiponectin in each fraction was detected through ELISA as employed in the aforementioned 1-2) (FIG. 6).

3) Comparison of Ratios of HMW Level to the Total Level (HMWR)

Figure 7:
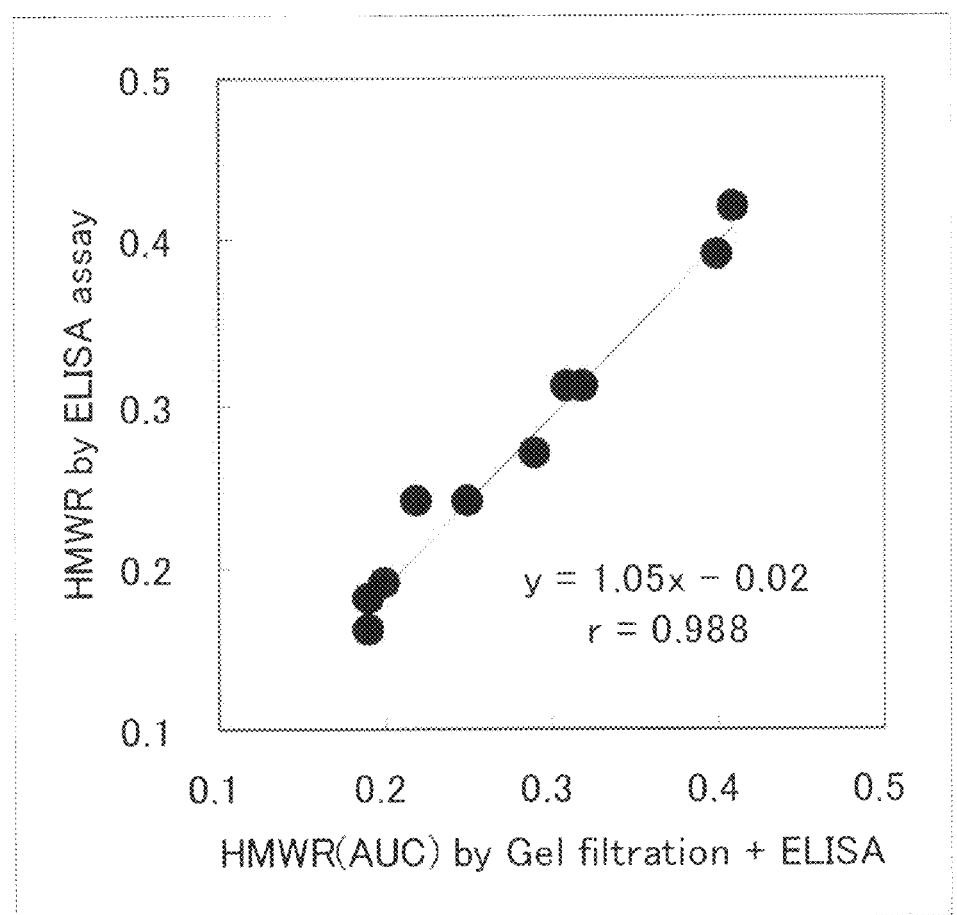
FIG. 7: A graph showing correlation between the HMW ratios computed by ELISA assay method and gel filtration separation method.

From the HMW levels and the total adiponectin levels obtained in 1-2), HMWRs were calculated. On the other hand, since the first peak of the three adiponectin elution peaks detected in 2) is attributed to HMW, the sum of the levels of the fractions was divided by the total level of the all adiponectin fractions, to thereby obtain an HMWR value. Through comparison of the HMWR values, the very strong correlation was observed between the values obtained through the two methods, and the HMWR values obtained through the two methods are almost equivalent (FIG. 7). Therefore, through treatment of a sample with chymotrypsin according to the present invention, the mouse HMW adiponectin can be correctly assayed in a very simple manner.

Example 5

Use of Chymotrypsin for Selective Assay of HMW Adiponectin in Human Serum

Figure 8:
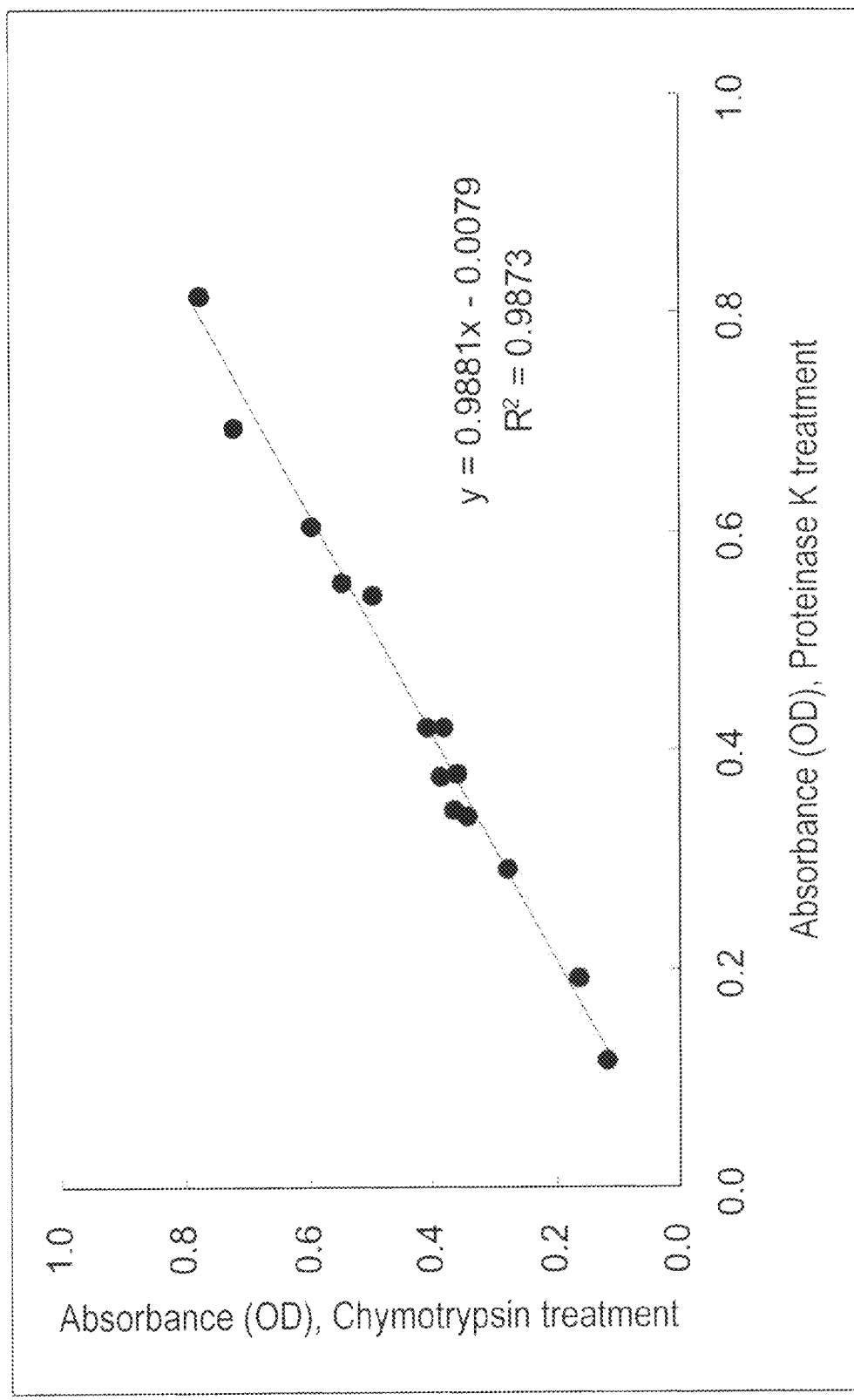
FIG. 8: A graph showing correlation between the results from assays of human-derived high-molecular-weight adiponectins treated by chymotrypsin and proteinase K.

A protease solution (50 mM Tris-HCl buffer, pH: 8.0) containing chymotrypsin (50 u/mL) (100 μL) was added to each human serum (n=14) (10 μL), and the mixture was incubated at 37° C. for 20 minutes. Then, a sample treatment solution (100 mM borate buffer, pH: 11.0) (700 μL) was added thereto, to thereby provide a treated sample solution for assaying human HMW. Instead of chymotrypsin, proteinase K (7.5 u/mL) was used as a control, and sample treatment was performed in the similar manner. Each treated sample solution was 10-fold diluted with BSA-PBST, and the adiponectin level of the sample was determined through the same method as employed in Example 3. The results are shown in FIG. 8.

The absorbances corresponding to levels of adiponectin remaining after treatment with proteinase K, which has been employed for selective assay of HMW adiponectin in human serum, almost completely equated to the absorbance measured after treatment with chymotrypsin. Therefore, chymotrypsin was found to be able to use in selective assay of HMW adiponectin in human serum.

The invention claimed is:

1. A method of measuring mouse high-molecular-weight adiponectin in a sample, the method comprising
reacting a sample, which comprises mouse adiponectin multimers with chymotrypsin to digest adiponectins other than the high-molecular weight adiponectin, and
measuring the higher molecular weight adiponectin remaining after the digestion with chymotrypsin in an immunological assay that comprise an anti-antiponecting antibody.

2. The method according to claim 1, wherein the sample is mouse serum or plasma.

3. The method according to claim 1, wherein the chymotrypsin is present in an amount of 0.1 to 1000 μ/ml.

4. The method according to claim 1, wherein the chymotrypsin is present in an amount of 0.1 to 100 μ/ml.

5. The method according to claim 1, wherein the immunological assay is a latex turbidimetric assay, an enzyme-linked immunosorbant assay, a chemiluminescent enzyme-linked immunosorbant assay, or a radioimmunoassay.

6. The method according to claim 1, wherein the immunological assay is a latex turbidmetric assay.

7. The method according to claim 1, wherein the anti-adiponectin antibody is immobilized on a solid carrier.

8. The method according to claim 1, wherein the chymotrypsin is α-chymotrypsin.

* * * * *